(12) United States Patent
Kapadia et al.

(10) Patent No.: US 12,114,950 B2
(45) Date of Patent: Oct. 15, 2024

(54) FOOT PEDAL ASSIGNMENT FOR ROBOTIC SURGICAL SYSTEMS

(71) Applicant: Covidien LP, Mansfield, MA (US)

(72) Inventors: Jaimeen Kapadia, Cambridge, MA (US); Eric J. Taylor, Southington, CT (US)

(73) Assignee: Covidien LP, Mansfield, MA (US)

(*) Notice: Subject to any disclaimer, the term of this patent is extended or adjusted under 35 U.S.C. 154(b) by 891 days.

(21) Appl. No.: 17/274,573

(22) PCT Filed: Sep. 10, 2019

(86) PCT No.: PCT/US2019/050274
§ 371 (c)(1),
(2) Date: Mar. 9, 2021

(87) PCT Pub. No.: WO2020/060793
PCT Pub. Date: Mar. 26, 2020

(65) Prior Publication Data
US 2022/0087759 A1    Mar. 24, 2022

Related U.S. Application Data

(60) Provisional application No. 62/732,134, filed on Sep. 17, 2018.

(51) Int. Cl.
*A61B 34/37* (2016.01)
*A61B 18/14* (2006.01)
(Continued)

(52) U.S. Cl.
CPC .............. *A61B 34/37* (2016.02); *A61B 18/14* (2013.01); *A61B 34/74* (2016.02); *A61B 90/37* (2016.02);
(Continued)

(58) Field of Classification Search
CPC .................... A61B 34/74; A61B 90/37; A61B 2017/00973; A61B 18/1233
See application file for complete search history.

(56) References Cited

U.S. PATENT DOCUMENTS 6,463,361 B1   10/2002  Wang et al.
8,828,023 B2    9/2014  Neff et al.
(Continued)

FOREIGN PATENT DOCUMENTS

EP    3628207 A1      4/2020
JP    2007509717 A    4/2007
(Continued)

OTHER PUBLICATIONS

Canadian Office Action dated Jul. 12, 2022 corresponding to counterpart Patent Application CA 3,110,704.
(Continued)

*Primary Examiner* — Sean W Collins
(74) *Attorney, Agent, or Firm* — Carter, DeLuca & Farrell LLP

(57) ABSTRACT

A method of automatically assigning foot pedals of a robotic surgical system to surgical instruments of a surgical robot of the robotic surgical system includes: receiving a signal that a first electrosurgical pedal is actuated; determining a number of electrosurgical instruments connected to the surgical robot in response to actuation of the first electrosurgical foot pedal; assigning the first electrosurgical foot pedal to a first electrosurgical instrument connected to the surgical robot after the first electrosurgical foot pedal is actuated; and delivering electrosurgical energy to the first electrosurgical instrument in response to actuation of the first electrosurgical foot pedal after assigning the first electrosurgical foot pedal to the first electrosurgical instrument.

20 Claims, 2 Drawing Sheets

(51) Int. Cl.
    *A61B 34/00*     (2016.01)
    *A61B 90/00*     (2016.01)
    *A61B 90/96*     (2016.01)
    *A61B 90/98*     (2016.01)
    *A61B 17/00*     (2006.01)
    *A61B 18/12*     (2006.01)

(52) U.S. Cl.
    CPC .............. *A61B 90/96* (2016.02); *A61B 90/98* (2016.02); *A61B 2017/00973* (2013.01); *A61B 18/1233* (2013.01); *A61B 2090/372* (2016.02)

(56) References Cited

U.S. PATENT DOCUMENTS

| | | | |
|---|---|---|---|
| 9,301,811 | B2 | 4/2016 | Goldberg et al. |
| 2005/0143724 | A1* | 6/2005 | El-Galley .......... A61B 18/1402 |
| | | | 606/34 |
| 2007/0185480 | A1 | 8/2007 | El-Galley et al. |
| 2007/0239028 | A1* | 10/2007 | Houser .................. A61B 34/71 |
| | | | 600/471 |
| 2008/0140158 | A1 | 6/2008 | Hamel et al. |
| 2009/0254109 | A1 | 10/2009 | Sekino et al. |
| 2012/0221147 | A1 | 8/2012 | Goldberg et al. |
| 2012/0283745 | A1 | 11/2012 | Goldberg et al. |
| 2014/0081455 | A1* | 3/2014 | Goldberg .............. A61B 90/98 |
| | | | 700/250 |
| 2015/0012134 | A1 | 1/2015 | Robinson et al. |
| 2015/0257814 | A1* | 9/2015 | Berry .................... A61B 34/74 |
| | | | 606/34 |
| 2015/0272657 | A1* | 10/2015 | Yates ................. A61B 18/1206 |
| | | | 606/34 |
| 2018/0280099 | A1 | 10/2018 | Cone et al. |
| 2019/0201023 | A1* | 7/2019 | Shelton, IV ....... A61B 18/1206 |
| 2020/0093552 | A1 | 3/2020 | Ishihara et al. |
| 2020/0205917 | A1 | 7/2020 | Peine et al. |

FOREIGN PATENT DOCUMENTS

| | | |
|---|---|---|
| JP | 2009247434 A | 10/2009 |
| JP | 2015534476 A | 12/2015 |
| WO | 2014154529 A1 | 10/2014 |
| WO | 2020060793 A1 | 3/2020 |

OTHER PUBLICATIONS

International Search Report mailed Dec. 30, 2019 and Written Opinion completed Dec. 30, 2019 corresponding to counterpart Int'l Patent Application PCT/US2019/050274.

Extended European Search Report dated May 20, 2022 corresponding to counterpart Patent Application EP 9861973.6.

Japanese Office Action mailed May 23, 2022 corresponding to counterpart Patent Application JP 2021-514117.

Australian Examination Report No. 1 dated Aug. 25, 2021 corresponding to counterpart Patent Application AU 2019345238.

Canadian Office Action dated Jan. 24, 2023, corresponding to counterpart Patent Application CA 3,110,704.

Chinese Office Action dated Apr. 15, 2023 for Chinese Patent Application No. 201980060582.3 (16 pages).

* cited by examiner

FOOT PEDAL ASSIGNMENT FOR ROBOTIC SURGICAL SYSTEMS

CROSS-REFERENCE TO RELATED APPLICATION

This application is a U.S. National Stage Application filed under 35 U.S.C. § 371(a) of International Patent Application Serial No. PCT/US2019/050274, filed Sep. 10, 2019, which claims the benefit of and priority to U.S. Provisional Patent Application Ser. No. 62/732,134, filed Sep. 17, 2018, the entire disclosure of each of which is incorporated by reference herein.

BACKGROUND

Robotic surgical systems have been used in minimally invasive medical procedures. During such a medical procedure, the robotic surgical system is controlled by a surgeon interfacing with a user interface. The user interface allows the surgeon to manipulate a surgical instrument that acts on a patient. The user interface includes a handle or gimbal that is moveable by the surgeon to control the robotic system. In some instances, an input of the user interface controls a function of a surgical instrument associated with one of the handles such as clamping of jaws, firing fasteners, firing a knife, delivering electrosurgical energy, etc. The input can be a foot pedal, a trigger, a button, or another suitable input.

During a medical procedure surgical instruments may be assigned to designated or selected foot pedals such that actuation of the assigned foot pedal actuates a particular surgical instrument. Generally, foot pedals are fixedly assigned to a surgical instrument operated by a respective input handle or are manually assigned by a clinician.

There is a continuing need for improved assigning of foot pedals, safeguards, and control of inputs with surgical instruments of robotic surgical systems.

SUMMARY

In an aspect of the present disclosure, a method of automatically assigning foot pedals of a robotic surgical system to surgical instruments of a surgical robot of the robotic surgical system includes receiving a signal that a first electrosurgical pedal is actuated, determining a number of electrosurgical instruments connected to the surgical robot in response to actuation of the first electrosurgical foot pedal, assigning the first electrosurgical foot pedal to a first electrosurgical instrument connected to the surgical robot after the first electrosurgical foot pedal is actuated, and delivering electrosurgical energy to the first electrosurgical instrument in response to actuation of the first electrosurgical foot pedal after assigning the first electrosurgical foot pedal to the first electrosurgical instrument.

In aspects, the method includes identifying a surgical instrument connected to the surgical robot as a fastener applying surgical instrument, automatically assigning a fastener foot pedal to the fastener applying surgical instrument, and generating a fastener fire command in response to each actuation of the fastener foot pedal such that a fastener is fired from the fastener applying surgical instrument for each actuation of the fastener foot pedal.

In some aspects, a generator of the surgical robot determines the number of electrosurgical instruments, assigns the first electrosurgical foot pedal, and/or delivers electrosurgical energy to the first electrosurgical instrument. Determining the number of electrosurgical instruments may include determining a single electrosurgical instrument is connected to the surgical robot and assigning the first electrosurgical foot pedal may include automatically assigning the first electrosurgical foot pedal to the first electrosurgical instrument in response to determining the single electrosurgical instrument is connected to the surgical robot.

In certain aspects, determining the number of electrosurgical instruments includes determining a first electrosurgical instrument and a second electrosurgical instrument are connected to the surgical robot. The method may include generating a first prompt for a clinician interfacing with the robotic surgical system to select one of the first or second electrosurgical instruments to assign to the first electrosurgical foot pedal in response to actuation of the first electrosurgical foot pod. The method may include receiving a selection of the first electrosurgical instrument from the clinician and assigning the first electrosurgical foot pedal to the first electrosurgical instrument in response to receiving the selection of the first electrosurgical instrument and before generating the first electrosurgical fire command.

In particular aspects, the method may include assigning the second electrosurgical foot pedal to the second electrosurgical instrument in response to receiving the selection of the first electrosurgical instrument. The method may include receiving a signal that the second electrosurgical foot pedal is actuated and delivering electrosurgical energy to the second electrosurgical instrument in response to actuation of the second electrosurgical foot pedal after assigning the second electrosurgical foot pedal to the second electrosurgical instrument.

In particular aspects, the method includes determining that the number of electrosurgical instruments includes determining a third electrosurgical instrument is connected to the surgical robot. Generating the first prompt may include allowing the clinician to select one of the first, second, or third electrosurgical instruments and the method may include generating a second prompt for a clinician interfacing with the robotic surgical system to select one of the second or third electrosurgical instruments to assign to the second electrosurgical foot pedal in response to receiving the selection of the first electrosurgical instrument from the clinician. The method may include receiving a selection of the second electrosurgical instrument from the clinician and assigning the second electrosurgical foot pedal to the second electrosurgical instrument in response to receiving the selection of the second electrosurgical instrument and before generating the first electrosurgical fire command.

In some aspects, the method includes regenerating the first prompt when delivering electrosurgical energy to the first electrosurgical instrument fails. The method may include verifying a condition of the first electrosurgical instrument before delivering electrosurgical energy to the first electrosurgical instrument. Verifying the condition of the first electrosurgical instrument may include verifying that the first electrosurgical instrument detects a ground path and that a circuit is closed with the ground path. Verifying the condition of the first electrosurgical instrument may include verifying a circuit is closed between electrodes of the first electrosurgical instrument, impedance between the electrodes in in a desired range, and that the electrodes are in a desired position. Verifying the condition of the first electrosurgical instrument may include verifying that jaw members of first electrosurgical instrument are in a clamped position.

In particular aspects, the method includes deassigning the first electrosurgical foot pedal from the first electrosurgical instrument in response to failing to verify the condition of the first electrosurgical instrument such that electrosurgical energy is prevented from being delivered to the first electrosurgical instrument.

In another aspect of the present disclosure, a robotic surgical system includes a surgical robot, a user console, a processing unit, and an electrosurgical generator. The surgical robot includes a first electrosurgical instrument and a second electrosurgical instrument. The user console includes a first foot pedal and a second foot pedal. The processing unit is configured to receive user commands from the user console and to control the surgical robot in response to the user commands. The electrosurgical generator is in electrical communication with the first and second electrosurgical instruments and is configured to assign one of the first or second electrosurgical instruments to the first foot pedal in response to actuation of the first foot pedal and/or to deliver electrosurgical energy to the assigned one of the first or second electrosurgical instruments in response to actuation of the first foot pedal.

In aspects, the surgical robot may include an arm that supports the first electrosurgical instrument and the electrosurgical generator may be positioned on the arm. The electrosurgical generator may be configured to deliver electrosurgical energy to the other of the first or second electrosurgical instrument in response to actuation of the second foot pedal.

In some aspects, the electrosurgical generator may be configured to generate a prompt on the user console in response to actuation of the first foot pedal when the first foot pedal is unassigned. The surgical robot may include a fastener applying surgical instrument and the user console may include a third foot pedal. The processing unit may be configured to assign the third foot pedal to the fastener applying surgical instrument in response to actuation of the third foot pedal such that the fastener applying surgical instrument fires a fastener in response to each actuation of the third foot pedal.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
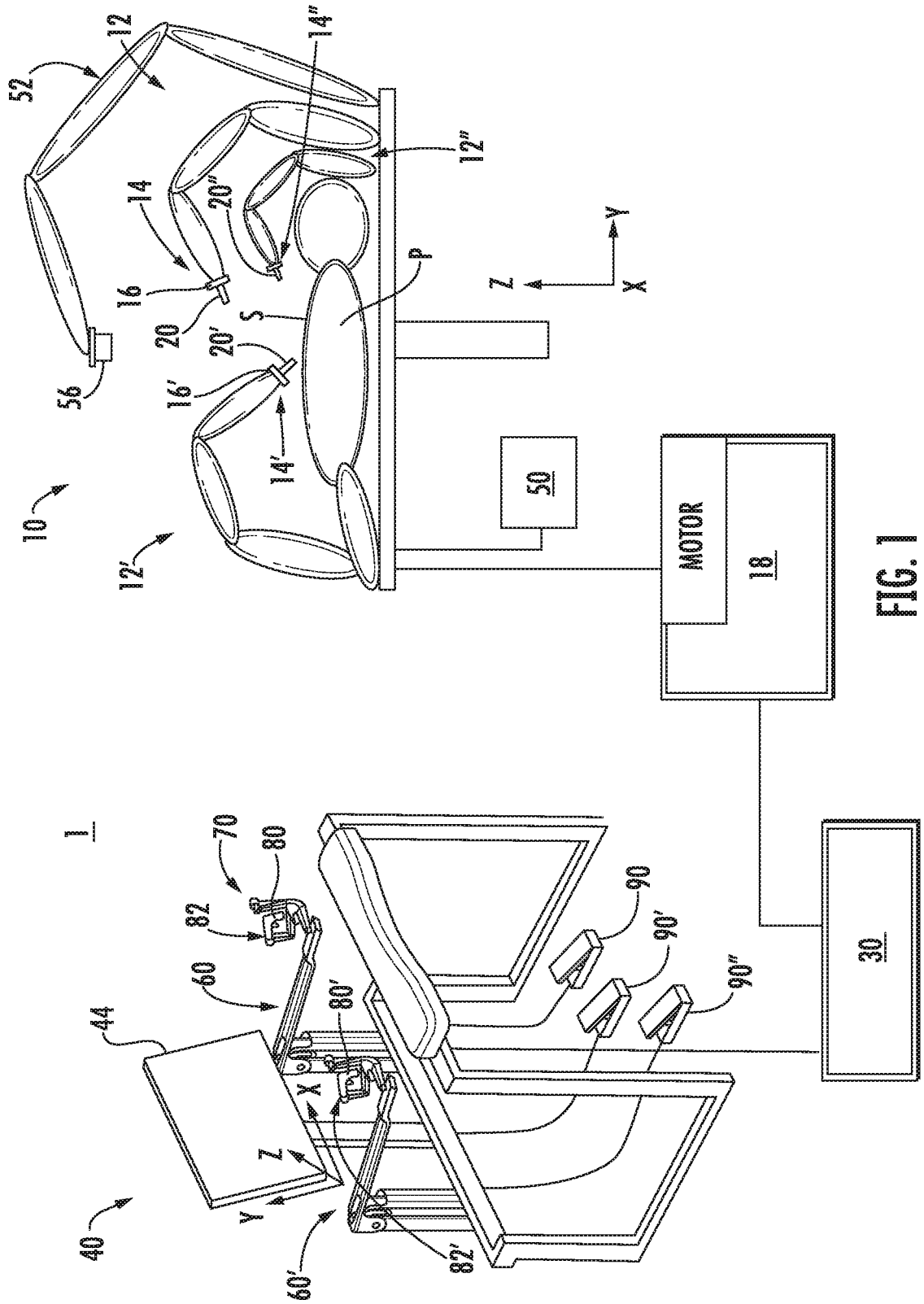
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, a staff member, or any other care provider and may include support personnel. Throughout this description, the term "proximal" refers to the portion of the device or component thereof that is closest to the clinician or farthest from the patient and the term "distal" refers to the portion of the device or component thereof that is farthest from the clinician or closest to the patient.

The present disclosure relates generally to methods and control systems for automatically assigning foot pedals to surgical instruments of a robotic surgical system. The method includes designating a foot pedal of a user interface as a fastener applying foot pedal such that when a fastener applying surgical instrument is connected to an arm of a surgical robot of the robotic surgical system, the fastener applying foot pedal is automatically assigned to the fastener applying surgical instrument. When the fastener applying foot pedal is assigned to the fastener applying surgical instrument, actuation of the fastener applying foot pedal fires a fastener from the fastener applying surgical instrument. In addition, the method includes designating foot pedals of the user interface as a first electrosurgical foot pedal and/or a second electrosurgical foot pedal and assigning the first and/or second electrosurgical foot pedals to electrosurgical instruments connected to an arm of the surgical robot. The assignment of one or both of the first and second electrosurgical foot pedals may be automatic when the one of the first or second electrosurgical foot pedals is actuated.

Referring to FIG. 1, a robotic surgical system 1 is shown generally as a surgical robot 10, a processing unit 30, and a user interface 40. The surgical robot 10 generally includes linkages 12, 12', 12" and a robot base 18. The linkages 12, 12', 12" moveably support surgical instruments or tools 20, 20', 20" which are configured to act on tissue. The linkages 12, 12', 12" may be in the form of arms each having an end 14 that supports a surgical instrument or tool 20, 20', 20" which is configured to act on tissue. When one or more of the surgical instruments 20, 20', 20" is an electrosurgical instrument, e.g., monopolar, bipolar, or LigaSure™ instrument, the surgical robot 10 may include an electrosurgical generator 50 configured to provide electrosurgical energy to the surgical instruments 20, 20', 20". The electrosurgical generator 50 may be integrated into one of the linkages 12, 12', 12" of the surgical robot 10. In addition, the ends 14 of the linkages 12, 12', 12" may include an imaging device 16 for imaging a surgical site "S". The ends 14 of the linkages 12, 12', 12" may include a tool detection system that identifies a type of surgical instrument supported or attached to the end 14, 14', 14" of the linkage 12, 12', 12". The user interface 40 is in communication with robot base 18 through the processing unit 30.

The user interface 40 includes a display device 44 which is configured to display images of the surgical site "S" which may include data captured by imaging devices 16 positioned on the ends 14 of the linkages 12, 12', 12" and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infrared images, ultrasound images, X-ray images, thermal images, and/or any other known real-time images of the surgical site "S". The imaging devices transmit captured imaging data to the processing unit 30 which creates images (e.g., three-dimensional images) of the surgical site "S" in real-time from the imaging data and transmits the images to the display device 44 for display.

The user interface 40 also includes control arms 60, 60' that support input handles 80, 80' attached to gimbals 70 which allow a clinician to manipulate the robotic system 10

(e.g., move the linkages 12, 12', 12", the ends 14 of the linkages 12, 12', 12", and/or the surgical instruments 20, 20', 20"). Each of the gimbals 70 is in communication with the processing unit 30 to transmit control signals thereto and to receive feedback signals therefrom. Additionally or alternatively, each of the input handles 80, 80' may include control interfaces which allow the surgeon to actuate (e.g., clamp, grasp, fire, open, close, rotate, thrust, slice, etc.) the surgical instruments 20, 20', 20" supported at the ends 14 of the linkages 12, 12', 12". The user interface 40 further includes foot pedals 90, 90', 90" that may be used with one or both of the input handles 80, 80' to activate functions of the surgical instruments 20, 20', 20".

Each of the gimbals 70 is moveable to move the ends 14 of the linkages 12, 12', 12" within a surgical site "S". The three-dimensional images on the display device 44 are orientated such that movement of the gimbals 70 moves the ends 14 of the linkages 12, 12', 12" as viewed on the display device 44. It will be appreciated that the orientation of the three-dimensional images on the display device 44 may be mirrored or rotated relative to a view from above the patient "P". In addition, it will be appreciated that the size of the three-dimensional images on the display device 44 may be scaled to be larger or smaller than the actual structures of the surgical site "S" permitting the surgeon to have a better view of structures within the surgical site "S". As the gimbal 70 is moved, the surgical instruments 20, 20', 20" are moved within the surgical site "S". Movement of the surgical instruments 20, 20', 20" may also include movement of the ends 14 of the linkages 12, 12', 12" which support the surgical instruments 20, 20', 20".

For a detailed discussion of the construction and operation of a robotic surgical system 1, reference may be made to U.S. Pat. No. 8,828,023, the entire contents of which are incorporated herein by reference.

The foot pedals 90, 90', 90" may be used to control actuation or firing of one or more of the surgical instruments 20, 20', 20". Each of the surgical instruments 20, 20', 20" may be a fastener applying surgical instrument and configured to apply fasteners to tissue, e.g., a stapler or a clip applier, or may be an electrosurgical instrument and configured to deliver electrosurgical energy to tissue, e.g., monopolar, bipolar, optical, or other electrothermal vessel sealing (e.g., LigaSure™, Medtronic, Inc.) electrosurgical instruments. To fire the surgical instruments 20, 20', 20", it is necessary to assign one of the foot pedals 90, 90', 90" to a respective one of the surgical instruments 20, 20', 20" to control the firing of the respective surgical instrument 20, 20', 20" in response to actuation of the assigned foot pedal. The user console 40 may include multiple rows of foot pedals such that a top row of foot pedals (not explicitly shown) may control a first mode of respective surgical instruments and a bottom row of foot pedals may control a second mode of the respective surgical instruments. For example, the top row of foot pedals may control the surgical instruments in a first mode of electrocautery, e.g., monopolar, and the bottom row of foot pedals may control the surgical instrument in a second mod of electrocautery, e.g., bipolar.

Previous solutions to assigning the foot pedals 90, 90', 90" have included manually assigning the foot pedals 90, 90', 90" within a user interface on the display 44 before a medical procedure, utilizing controls of the input handles 80, 80' to assign a foot pedal 90, 90', 90", and/or including a separate foot pedal for each surgical instrument. Examples of these solutions for assigning foot pedals are disclosed in International Patent Applications PCT/US2018/033080, PCT/US2018/033084, and PCT/US2018/033097 which were each filed May 17, 2018. The entire contents of each of these applications are hereby incorporated by reference.

Figure 2:
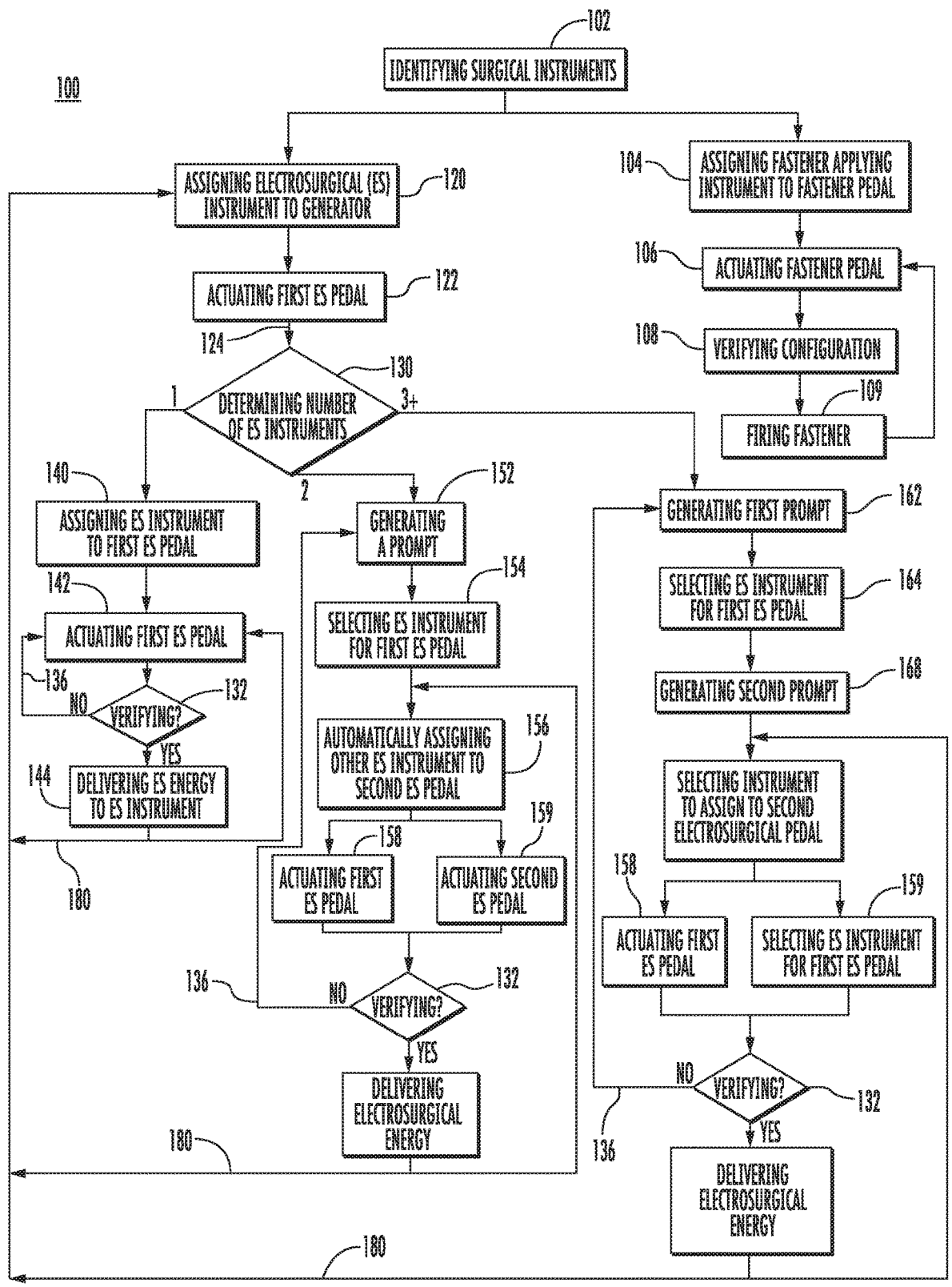
FIG. 2 is a flowchart illustrating a method of automatically assigning foot pedals to surgical instruments of the robotic system of FIG. 1.

Referring to FIG. 2, a method 100 of automatically assigning the foot pedals 90, 90', 90" to the surgical instruments 20, 20', 20" is disclosed in accordance with the present disclosure with reference to the robotic surgical system of FIG. 1. Initially, one of the foot pedals 90, 90', 90" may be designated as a fastener foot pedal, e.g., foot pedal 90", and the other two foot pedals may be designated as electrosurgical foot pedals, e.g., foot pedals 90, 90'. In addition, one or more surgical instruments 20, 20', 20" are coupled or connected to the linkages 12, 12', 12". When the surgical instruments 20, 20', 20" are connected to the linkages 12, 12', 12", the surgical robot 10 and/or the processing unit 30 interrogates or identifies a type of each of the surgical instruments 20, 20', 20", e.g., electrosurgical, fastener applying, or non-firing (Step 102).

For example if the connected surgical instrument 20" is a fastener applying surgical instrument, e.g., a stapler or a clip applier, the processing unit 30 assigns the fastener applying surgical instrument 20" to the fastener foot pedal 90" (Step 104). When the fastener applying surgical instrument 20" is assigned to the fastener foot pedal 90", a fastener fire command is sent to the surgical robot 10, from the processing unit 30, to fire the fastener applying surgical instrument 20" when the fastener foot pedal 90" is actuated (Step 106). In response to the fastener fire command, the fastener applying surgical instrument 20" is fired (Step 109). In some embodiments, the method 100 includes the surgical robot 10 and/or the processor unit 30 verifying a configuration of the fastener applying surgical instrument 20", e.g., that jaws of the surgical instrument are in a closed or clamped position, before sending the fastener fire command and/or firing the fastener applying surgical instrument 20" (Step 108).

If the connected surgical instrument is an electrosurgical instrument, e.g., surgical instrument 20, 20', the processing unit 30 assigns the electrosurgical instrument 20, 20' to the electrosurgical generator 50 to assign the surgical instrument to one of the electrosurgical foot pedals 90, 90' (Step 120). During a medical procedure, when a first one of the electrosurgical foot pedals, e.g., foot pedal 90, is actuated (Step 122), an electrosurgical fire command is sent to the electrosurgical generator 50 (Step 124). In response to the electrosurgical fire command, the electrosurgical generator 50 determines the number of electrosurgical instruments connected to the surgical robot 10 (Step 130). The electrosurgical generator 50 may determine the number and type of surgical instruments by interrogating the surgical robot 10. Additionally or alternatively, the electrosurgical generator 50 may include an RFID identification system, may include a barcode scanner that scans each surgical instrument as it is connected, and/or may utilize one or more cameras, e.g., camera 56, to identify the surgical instruments.

When a single electrosurgical instrument, e.g., surgical instrument 20, is connected to the surgical robot 10, the electrosurgical generator 50 assigns the electrosurgical instrument 20 to the electrosurgical foot pedal 90 (Step 140) and delivers electrosurgical energy to the electrosurgical instrument 20 in response to each actuation of the electrosurgical foot pedal 90 (Step 142). The electrosurgical generator 50 may deliver electrosurgical ener+gy (Step 144) with the first actuation of the electrosurgical foot pedal 90 and each subsequent actuation of the electrosurgical foot pedal 90. Alternatively, the electrosurgical generator 50 may assign the electrosurgical instrument 20 to the first actuation of the electrosurgical foot pedal 90 and deliver electrosurgical energy with each subsequent actuation of the electrosurgical foot pedal 90. The electrosurgical foot pedal 90 remains assigned with the electrosurgical instrument 20 until the surgical instruments connected to the surgical robot 10 changes (Step 180) or until the electrosurgical instrument 20 fails to fire in response to actuation of the electrosurgical foot pedal 90 (Step 136).

Before delivering electrosurgical energy to an assigned electrosurgical instrument 20, the generator 50 may verify one or more conditions of the electrosurgical instrument 20 (Step 132). The conditions of the electrosurgical instrument 20 may be dependent on the type of electrosurgical instrument 20. Specifically, when the electrosurgical instrument 20 is a monopolar instrument, the generator 50 may verify that a ground path is detected and that the circuit is closed with the ground path before delivering electrosurgical energy to the monopolar instrument. When the electrosurgical instrument 20 is a bipolar instrument, the generator 50 may verify that a circuit is closed between the electrodes, that an impedance between the electrodes is in an desired range, and/or that electrodes of the bipolar instrument are in a desired position, e.g., that jaw members are in a closed or clamped position before delivering electrosurgical energy to the bipolar instrument. When the electrosurgical instrument 20 is an electrothermal vessel sealing instrument, the generator 50 may verify that jaw members of the electrothermal vessel sealing instrument are in a desired position, e.g., a closed or clamped position, before delivering electrosurgical energy to the electrothermal vessel sealing instrument. In addition, the generator 50 and/or the surgical robot 10 may verify a depth of insertion of the electrosurgical instrument 20 before delivering electrosurgical energy to the electrosurgical instrument 20.

When a first electrosurgical instrument, e.g., surgical instrument 20, and a second electrosurgical instrument, e.g., surgical instrument 20', are connected to the surgical robot 10, actuation of the first electrosurgical foot pedal 90 generates a prompt on the display 44 for the clinician to select an electrosurgical instrument, e.g., surgical instrument 20, 20', to assign to the first electrosurgical foot pedal 90 (Step 152). The prompt may be generated by the processing unit 30 or the generator 50. The clinician utilizes the user interface 20 to select which one of first or second electrosurgical instruments 20, 20' to assign to the first electrosurgical foot pedal 90 (Step 154). To select which one of the first or second electrosurgical instruments 20, 20' to assign to the first electrosurgical foot pedal 90, the clinician may pull a trigger of an input handle, e.g., input handle 80, associated with the corresponding electrosurgical instrument 20, 20' or the clinician may select the first or second electrosurgical instrument 20, 20' on the display 44 by interfacing with a graphical user interface of the display 44, e.g., touching the display 44 or using a controller to select an item on the display 44. When the first electrosurgical foot pedal 90 is assigned to one of the first or second electrosurgical instruments 20, 20', the electrosurgical generator 50 delivers electrosurgical energy to the assigned first or second electrosurgical instrument 20, 20' in response to each actuation of the first electrosurgical foot pedal 90 (Step 158).

After the first electrosurgical pedal 90 is assigned to the one of the first or second electrosurgical instrument 20, 20', the generator 50 automatically assigns the other of the first or second electrosurgical instruments 20, 20' to the second electrosurgical pedal 90' (Step 156). When the second electrosurgical foot pedal 90' is actuated, the generator 50 delivers electrosurgical energy to the other of the first or second electrosurgical instrument 20, 20' (Step 159).

Before the electrosurgical energy is delivered to either the first or second electrosurgical instruments 20, 20', the generator 50 may perform the verifications as detailed above before each delivery of electrosurgical energy (Step 132). Further, the first and second electrosurgical foot pedals 90, 90' stay assigned until the surgical instruments connected to the surgical robot 10 change (Step 180) or until one of the electrosurgical instruments 20, 20' fails to fire in response to actuation of the electrosurgical foot pedal 90 (Step 136). In addition, during a medical procedure, if the clinician wants to manually reassign the first or second electrosurgical foot pedal 90, 90' to a different surgical instrument, the clinician may double tap either of the first or second electrosurgical foot pedals 90, 90' to reopen the prompt on the display 44 as detailed above (Step 160). As detailed above, the prompt is displayed on the display 44; however, the prompt may be displayed on different displays including, but not limited to, a heads up display (not shown).

When a first electrosurgical instrument, e.g., surgical instrument 20, a second electrosurgical instrument, e.g., surgical instrument 20', and a third electrosurgical instrument, e.g., surgical instrument 20", are connected to the surgical robot 10, actuation of the first electrosurgical foot pedal 90 generates a first prompt on the display 44 for the clinician to select an electrosurgical instrument, e.g., surgical instrument 20, 20', 20", to assign to the first electrosurgical foot pedal 90 (Step 162). The first prompt may be generated by the processing unit 30 or the generator 50. The clinician utilizes the user interface 20 to select which one of first, second, or third electrosurgical instruments 20, 20', 20" to assign to the first electrosurgical foot pedal 90 (Step 164). To select which one of the first, second, or third electrosurgical instruments 20, 20', 20" to assign to the first electrosurgical foot pedal 90, the clinician may pull a trigger of an input handle, e.g., input handle 80, assigned with the corresponding electrosurgical instrument 20, 20', 20" or the clinician may select the first, second, or third electrosurgical instrument 20, 20', 20" on the display 44 by interfacing with a graphical user interface of the display 44, e.g., touching the display 44 or using a controller to select an item on the display 44. When the first electrosurgical foot pedal 90 is assigned to one of the first, second, or third electrosurgical instrument 20, 20', 20", the electrosurgical generator 50 delivers electrosurgical energy to the assigned first, second, or third electrosurgical instrument 20, 20', 20" in response to each actuation of the first electrosurgical foot pedal 90 (Step 166).

After the first electrosurgical pedal 90 is assigned to one of the first, second, or third electrosurgical instrument 20, 20', 20", the processing unit 30 or the generator 50 generates a second prompt on the display 44 for the clinician to select which one of the other of the first, second, or third electrosurgical instruments 20, 20', 20" to assign to the second electrosurgical pedal 90' (Step 168). To select which one of the first, second, or third electrosurgical instruments 20, 20', 20" to assign to the second electrosurgical foot pedal 90', the clinician may pull a trigger of an input handle, e.g., input handle 80', associated with the corresponding electrosurgical instrument 20, 20', 20" or the clinician may select the first, second, or third electrosurgical instrument 20, 20', 20" on the display 44 by interfacing with a graphical user interface of the display 44. When the second electrosurgical foot pedal 90' is assigned with the other of the first, second, or third electrosurgical instrument 20, 20', 20", the electrosurgical generator 50 delivers electrosurgical energy to the assigned first, second, or third electrosurgical instrument 20, 20', 20" in response to each actuation of the second electrosurgical foot pedal 90' (Step 169).

Before the electrosurgical energy is delivered to either the first, second, or third electrosurgical instrument 20, 20', 20", the generator 50 may perform the verifications as detailed above (Step 132). The first and second electrosurgical foot pedals 90, 90' stay assigned until the surgical instruments connected to the surgical robot 10 change (Step 180) or until the assigned first, second, or third electrosurgical instrument 20, 20', 20" fails to fire in response to actuation of the respective electrosurgical foot pedal 90, 90' (Step 136). In addition, during a medical procedure, if the clinician wants to manually reassign the first or second electrosurgical foot pedal 90, 90' to a different surgical instrument, the clinician may double tap either of the first or second electrosurgical foot pedals 90, 90' to reopen the prompt on the display 44 as detailed above (Step 160). As detailed above, the prompt is displayed on the display 44; however, the prompt may be displayed on different displays including, but not limited to, a heads up display (not shown).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method automatically assigning foot pedals of a robotic surgical system to surgical instruments of a surgical robot of the robotic surgical system, the method comprising:
   receiving a signal that a first electrosurgical foot pedal is actuated;
   determining a number of electrosurgical instruments connected to the surgical robot in response to actuation of the first electrosurgical foot pedal connected to the surgical robot;
   assigning the first electrosurgical foot pedal to a first electrosurgical instrument connected to the surgical robot after the first electrosurgical foot pedal is actuated;
   automatically assigning a second electrosurgical foot pedal to a second electrosurgical instrument connected to the surgical robot in response to assigning the first electrosurgical foot pedal to the first electrosurgical instrument; and
   delivering electrosurgical energy to the first electrosurgical instrument in response to actuation of the first electrosurgical foot pedal after assigning the first electrosurgical foot pedal to the first electrosurgical instrument.

2. The method according to claim 1, further comprising:
   identifying a fastener applying surgical instrument connected to the surgical robot;
   automatically assigning a fastener foot pedal to the fastener applying surgical instrument; and
   generating a fastener fire command in response to each actuation of the fastener foot pedal such that a fastener is fired from the fastener applying surgical instrument for each actuation of the fastener foot pedal.

3. The method according to claim 1, wherein a generator of the surgical robot performs at least one of determining the number of electrosurgical instruments, assigning the first electrosurgical foot pedal, or delivering electrosurgical energy to the first electrosurgical instrument.

4. The method according to claim 1, further comprising:
   disconnecting the second electrosurgical instrument from the surgical robot;
   determining a single electrosurgical instrument is connected to the surgical robot; and
   automatically assigning the first electrosurgical foot pedal to the first electrosurgical instrument in response to determining the single electrosurgical instrument is connected to the surgical robot.

5. The method according to claim 1, further comprising:
   generating a first prompt for a clinician interfacing with the robotic surgical system to select one of the first or second electrosurgical instruments to assign to the first electrosurgical foot pedal in response to actuation of the first electrosurgical foot pedal;
   receiving a selection of the first electrosurgical instrument from the clinician; and
   assigning the first electrosurgical foot pedal to the first electrosurgical instrument in response to receiving the selection of the first electrosurgical instrument and before generating a first electrosurgical fire command.

6. The method according to claim 5, further comprising receiving a signal that the second electrosurgical foot pedal is actuated and delivering electrosurgical energy to the second electrosurgical instrument in response to actuation of the second electrosurgical foot pedal after assigning the second electrosurgical foot pedal to the second electrosurgical instrument.

7. The method according to claim 5, wherein determining the number of electrosurgical instruments includes determining a third electrosurgical instrument is connected to the surgical robot, and wherein the first prompt includes allowing the clinician to select one of the first, second, or third electrosurgical instruments and wherein the method further comprises:
   generating a second prompt for a clinician interfacing with the robotic surgical system to select one of the second or third electrosurgical instruments to assign to the second electrosurgical foot pedal in response to receiving the selection of the first electrosurgical instrument from the clinician;
   receiving a selection of the second electrosurgical instrument from the clinician; and
   assigning the second electrosurgical foot pedal to the second electrosurgical instrument in response to receiving the selection of the second electrosurgical instrument and before generating the first electrosurgical fire command.

8. The method according to claim 5, further comprising regenerating the first prompt when delivering electrosurgical energy to the first electrosurgical instrument fails.

9. The method according to claim 1, further comprising verifying a condition of the first electrosurgical instrument before delivering electrosurgical energy to the first electrosurgical instrument.

10. The method according to claim 9, wherein verifying the condition of the first electrosurgical instrument includes verifying the first electrosurgical instrument detects a ground path and that a circuit is closed with the ground path.

11. The method according to claim 9, wherein verifying the condition of the first electrosurgical instrument includes at least one of verifying a circuit is closed between electrodes of the first electrosurgical instrument, verifying impedance between the electrodes is in a desired range, or verifying that the electrodes are in a desired position.

12. The method according to claim 9, wherein verifying the condition of the first electrosurgical instrument includes verifying that jaw members of the first electrosurgical instrument are in a clamped position.

13. The method according to claim 9, further comprising deassigning the first electrosurgical foot pedal from the first electrosurgical instrument in response to failing to verify the condition of the first electrosurgical instrument such that electrosurgical energy is prevented from being delivered to the first electrosurgical instrument.

14. A robotic surgical system comprising:
a surgical robot including a first electrosurgical instrument and a second electrosurgical instrument;
a user console including a first foot pedal and a second foot pedal;
a processing unit configured to receive user commands from the user console and to control the surgical robot in response to the user commands; and
an electrosurgical generator in electrical communication with the first and second electrosurgical instruments, the electrosurgical generator configured to at least one of assign one of the first or second electrosurgical instruments to the first foot pedal in response to actuation of the first foot pedal or to deliver electrosurgical energy to the assigned one of the first or second electrosurgical instruments in response to actuation of the first foot pedal,
wherein the electrosurgical generator is configured to automatically assign a second foot pedal to the second electrosurgical instrument in response to assigning the first foot pedal to the first electrosurgical instrument.

15. The robotic surgical system according to claim 14, wherein the surgical robot includes an arm that supports the first electrosurgical instrument, and wherein the electrosurgical generator is positioned on the arm.

16. The robotic surgical system according to claim 14, wherein the electrosurgical generator is configured to deliver electrosurgical energy to the other of the first or second electrosurgical instrument in response to actuation of the second foot pedal.

17. The robotic surgical system according to claim 14, wherein the electrosurgical generator is configured to generate a prompt on the user console in response to actuation of the first foot pedal when the first foot pedal is unassigned.

18. The robotic surgical system according to claim 14, wherein the surgical robot includes a fastener applying surgical instrument and the user console includes a third foot pedal, the processing unit configured to assign the third foot pedal to the fastener applying surgical instrument in response to actuation of the third foot pedal such that the fastener applying surgical instrument fires a fastener in response to each actuation of the third foot pedal.

19. The robotic surgical system according to claim 14, wherein the user console further includes a first row of pedals configured to control a first mode of one of the first or second electrosurgical instruments, and a second row of pedals configured to control a second mode of one of the first or second electrosurgical instruments.

20. A method automatically assigning foot pedals of a robotic surgical system to surgical instruments of a surgical robot of the robotic surgical system, the method comprising:
determining a first electrosurgical instrument and a second electrosurgical instrument are connected to the surgical robot in response to actuation of a first electrosurgical foot pedal connected to the surgical robot;
generating a first prompt for a clinician interfacing with the robotic surgical system to select one of the first or second electrosurgical instruments to assign to the first electrosurgical foot pedal in response to actuation of the first electrosurgical foot pedal;
receiving a selection of the first electrosurgical instrument from the clinician;
assigning the first electrosurgical foot pedal to the first electrosurgical instrument in response to receiving the selection of the first electrosurgical instrument after the first electrosurgical foot pedal is actuated and before generating a first electrosurgical fire command;
delivering electrosurgical energy to the first electrosurgical instrument in response to actuation of the first electrosurgical foot pedal after assigning the first electrosurgical foot pedal to the first electrosurgical instrument; and
regenerating the first prompt when delivering electrosurgical energy to the first electrosurgical instrument fails.

* * * * *